(12) United States Patent
Luborsky et al.

(10) Patent No.: US 8,722,351 B2
(45) Date of Patent: May 13, 2014

(54) DIAGNOSTIC TESTS FOR ABNORMAL OVARIAN CONDITIONS

(75) Inventors: Judith Luborsky, Riverside, IL (US); Seby Edassery, Skokie, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 13/496,418

(22) PCT Filed: Sep. 17, 2010

(86) PCT No.: PCT/US2010/049245
§ 371 (c)(1),
(2), (4) Date: Jun. 5, 2012

(87) PCT Pub. No.: WO2011/035101
PCT Pub. Date: Mar. 24, 2011

(65) Prior Publication Data
US 2012/0252036 A1    Oct. 4, 2012

Related U.S. Application Data

(60) Provisional application No. 61/243,247, filed on Sep. 17, 2009.

(51) Int. Cl.
G01N 33/574    (2006.01)

(52) U.S. Cl.
USPC .......................................... 435/7.23; 435/7.1

(58) Field of Classification Search
None
See application file for complete search history.

(56) References Cited

U.S. PATENT DOCUMENTS

| 5,914,257 A * | 6/1999 | Fukaya et al. ............... 435/190 |
| 2002/0001805 A1 | 1/2002 | Roden et al. |
| 2002/0042066 A1 | 4/2002 | Bandman et al. |

OTHER PUBLICATIONS

Barua et al, Am J Reprod Immunol 57:243-9, 2007, item AC in IDS filed Jun. 5, 2012.*
Gagnon et al, Clin Cancer Res 14: 764-771, 2008.*
Huang et al , Int J Can 118:2433-2440, 2006.*
Barua et al., "Anti-tumor and anti-ovarian autoantibodies in women with ovarian cancer," *Am. J. Reprod. Immunol.*, 57(4): 243-249 (2007).
Edassery et al., "Autoantigens in ovarian autoimmunity associated with unexplained infertility and premature ovarian failure," *Fertil. Steril.*, 94(7): 2636-2641 (2010).
Huang et al., "Selenium binding protein 1 in ovarian cancer," *Int. J. Cancer*, 118(10): 2433-2440 (2006).
Stammer et al., "Selenium-binding Protein 1 expression in ovaries and ovarian tumors in the laying hen, a spontaneous model of human ovarian cancer," *Gynecologic Oncol.*, 109(1): 115-121 (2008).
Search Report and Written Opinion issued in Int'l App. No. PCT/US2010/049245 (2010).

* cited by examiner

*Primary Examiner* — Lei Yao
(74) *Attorney, Agent, or Firm* — Barnes & Thornburg LLP; Alice O. Martin

(57) ABSTRACT

Methods and compositions, and a kit for diagnosing ovarian disorders including autoimmunity and ovarian cancer. Ovarian autoimmunity is associated with unexplained infertility or idiopathic premature ovarian failure that occurs in the absence of polyglandular disease. Methods and composition described herein are used to detect ovarian autoimmunity before the onset of ovarian dysfunction. Thus, those individuals are identified who would benefit from therapy to maintain, as well as restore, ovarian function.

2 Claims, 14 Drawing Sheets

|  | Infertility/POF (n=28) | OvCa (n=21) | Benign (n=9) | Normal (n=6) |
|---|---|---|---|---|
| Negative | 32% | 43% | 67% | Ref |
| Positive | 68% | 57% | 33% | Ref |

FIG. 1

```
   1 caccagcaca gcaaacccgc cgggatcaaa gtgtaccagt cggcagcatg gctacgaaat
  61 gtgggaattg tggacccggc tactccaccc ctctggaggc catgaaagga cccagggaag
 121 agatcgtcta cctgccctgc atttaccgaa acacaggcac tgaggcccca gattatctgg
 181 ccactgtgga tgttgacccc aagtctcccc agtattgcca ggtcatccac cggctgccca
 241 tgcccaacct gaaggacgag ctgcatcact caggatggaa cacctgcagc agctgcttcg
 301 gtgatagcac caagtcgcgc accaagctgg tgctgcccag tctcatctcc tctcgcatct
 361 atgtggtgga cgtgggctct gagccccggg ccccaaagct gcacaaggtc attgagccca
 421 aggacatcca tgccaagtgc gaactggcct ttctccacac cagccactgc ctggccagcg
 481 gggaagtgat gatcagctcc ctgggagacg tcaagggcaa tggcaaaggg ggttttgtgc
 541 tgctggatgg ggagacgttc gaggtgaagg ggacatggga gagacctggg ggtgctgcac
 601 cgttgggcta tgacttctgg taccagcctc gacacaatgt catgatcagc actgagtggg
 661 cagctcccaa tgtcttacga gatggcttca accccgctga tgtggaggct ggactgtacg
 721 ggagccactt atatgtatgg gactggcagc gccatgagat tgtgcagacc ctgtctctaa
 781 aagatgggct tattcccttg gagatccgct tcctgcacaa cccagacgct gcccaaggct
 841 ttgtgggctg cgcactcagc tccaccatcc agcgcttcta caagaacgag ggaggtacat
 901 ggtcagtgga gaaggtgatc caggtgcccc ccaagaaagt gaagggctgg ctgctgcccg
 961 aaatgccagg cctgatcacc gacatcctgc tctccctgga cgaccgcttc ctctacttca
1021 gcaactggct gcatggggac ctgaggcagt atgacatctc tgacccacag agaccccgcc
1081 tcacaggaca gctcttcctc ggaggcagca ttgttaaggg aggccctgtg caagtgctgg
1141 aggacgagga actaaagtcc cagccagagc cctagtggt caagggaaaa cgggtggctg
1201 gaggccctca gatgatccag ctcagcctgg atgggaagcg cctctacatc accacgtcgc
1261 tgtacagtgc ctgggacaag cagttttacc ctgatctcat cagggaaggc tctgtgatgc
1321 tgcaggttga tgtagacaca gtaaaaggag ggctgaagtt gaaccccaac ttcctggtgg
1381 acttcgggaa ggagccccctt ggcccagccc ttgcccatga gctccgctac cctgggggcg
1441 attgtagctc tgacatctgg atttgaactc caccctcatc acccacactc cctatttgg
1501 gccctcactt ccttggggac ctggcttcat tctgctctct cttggcaccc gacccttggc
1561 agcatgtacc acacagccaa gctgagactg tggcaatgtg ttgagtcata tacatttact
1621 gaccactgtt gcttgttgct cactgtgctg cttttccatg agctcttgga ggcaccaaga
1681 aataaactcg taaccctgtc cttcaaaaaa aaaaaaaaa a(SEQ ID NO: 1)
```

FIG. 10

MATKC GNCGP GYSTP LEAMK GPREE IVYLP CIYRN TGTEA PDYLA TVDVD
PKSPQ YCQVI HRLPM PNLKD ELHHS GWNTC SSCFG DSTKS RTKLV LPSLI SSRIY
VVDVG SEPRA PKLHK VIEPK DIHAK CELAF LHTSH CLASG EVMIS SLGDV
KGNGK GGFVL LDGET FEVKG TWERP GGAAP LGYDF WYQPR HNVMI STEWA
APNVL RDGFN PADVE AGLYG SHLYV WDWQR HEIVQ TLSLK DGLIP LEIRF
LHNPD AAQGF VGCAL SSTIQ RFYKN EGGTW SVEKV IQVPP KKVKG WLLPE
MPGLI TDILL SLDDR FLYFS NWLHG DLRQY DISDP QRPRL TGQLF LGGSI
VKGGP VQVLE DEELK SQPEP LVVKG KRVAG GPQMI QLSLD GKRLY ITTSL
YSAWD KQFYP DLIRE GSVML QVDVD TVKGG LKLNP NFLVD FGKEP LGPAL
AHELR YPGGD CSSDI WI(SEQ ID NO: 2)

NCBI Reference Sequence for SELENBP1 : NM_003944
LOCUS NM_003944 1721 bp mRNA
DEFINITION: Homo sapiens selenium binding protein 1 (SELENBP1), mRNA.
ACCESSION NM_003944

FIG. 11

```
   1 atcagaacca aattgctgag ccagtcacct gtgttccagg agccgaatca gaaatgtcat
  61 cctcaggcac gccagactta cctgtcctac tcaccgattt gaagattcaa tatactaaga
 121 tcttcataaa caatgaatgg catgattcag tgagtggcaa gaaatttcct gtctttaatc
 181 ctgcaactga ggaggagctc tgccaggtag aagaaggaga taaggaggat gttgacaagg
 241 cagtgaaggc cgcaagacag gcttttcaga ttggatcccc gtggcgtact atggatgctt
 301 ccgagagggg gcgactatta tacaagttgg ctgatttaat cgaaagagat cgtctgctgc
 361 tggcgacaat ggagtcaatg aatggtggaa aactctattc caatgcatat ctgaatgatt
 421 tagcaggctg catcaaaaca ttgcgctact gtgcaggttg ggctgacaag atccagggcc
 481 gtacaatacc aattgatgga aatttttta catatacaag acatgaacct attggtgtat
 541 gtggccaaat cattccttgg aatttcccgt tggttatgct catttggaag atagggcctg
 601 cactgagctg tggaaacaca gtggttgtca aaccagcaga gcaaactcct ctcactgctc
 661 tccacgtggc atctttaata aaagaggcag ggtttcctcc tggagtagtg aatattgttc
 721 ctggttatgg gcctacagca ggggcagcca tttcttctca catggatata gacaaagtag
 781 ccttcacagg atcaacagag gttggcaagt tgatcaaaga agctgccggg aaaagcaatc
 841 tgaagagggt gaccctggag cttggaggaa agagcccttg cattgtgtta gctgatgccg
 901 acttggacaa tgctgttgaa tttgcacacc atggggtatt ctaccaccag gccagtgtt
 961 gtatagccgc atccaggatt tttgtggaag aatcaattta tgatgagttt gttcgaagga
1021 gtgttgagcg ggctaagaag tatatccttg gaaatcctct gaccccagga gtcactcaag
1081 gccctcagat tgacaaggaa caatatgata aaatacttga cctcattgag agtgggaaga
1141 aagaaggggc caaactggaa tgtggaggag gcccgtgggg gaataaaggc tactttgtcc
1201 agcccacagt gttctctaat gttacagatg agatgcgcat tgccaaagag gagattttg
1261 gaccagtgca gcaaatcatg aagtttaaat ctttagatga cgtgatcaaa agagcaaaca
1321 atactttcta tggcttatca gcaggagtgt ttaccaaaga cattgataaa gccataacaa
1381 tctcctctgc tctgcaggca ggaacagtgt gggtgaattg ctatggcgtg gtaagtgccc
1441 agtgcccctt tggtggattc aagatgtctg gaaatggaag agaactggga gagtacggtt
1501 tccatgaata tacagaggtc aaaacagtca cagtgaaaat ctctcagaag aactcataaa
1561 gaaaatacaa gagtggagag aagctcttca atagctaagc atctccttac agtcactaat
1621 atagtagatt ttaaagacaa aatttttctt ttcttgattt ttttaaacat aagctaaatc
1681 atattagtat taatactacc catagaaaac ttgacatgta gcttcttctg aaagaattat
1741 ttgccttctg aaatgtgacc cccaagtcct atcctaaata aaaaagaca aattcggatg
1801 tatgatctct ctagctttgt catagttatg tgattttcct ttgtagctac ttttgcagga
1861 taataatttt atagaaaagg aacagttgca tttagcttct ttcccttagt gactcttgaa
1921 gtacttaaca tacacgttaa ctgcagagta aattgctctg ttcccagtag ttataaagtc
1981 cttggactgt tttgaaaagt ttcctaggat gtcatgtctg cttgtcaaaa gaaataatcc
2041 ctgtaatatt tagctgtaaa ctgaatataa agcttaataa aaacaacctt gcatgaaaaa
2101 aaaaaaaaaa aaaaaa(SEQ ID NO: 3)
```

FIG. 12

MSSSG TPDLP VLLTD LKIQY TKIFI NNEWH DSVSG KKFPV FNPAT EEELC
QVEEG DKEDV DKAVK AARQA FQIGS PWRTM DASER GRLLY KLADL IERDR
LLLAT MESMN GGKLY SNAYL NDLAG CIKTL RYCAG WADKI QGRTI PIDGN
FFTYT RHEPI GVCGQ IIPWN FPLVM LIWKI GPALS CGNTV VVKPA EQTPL
TALHV ASLIK EAGFP PGVVN IVPGY GPTAG AAISS HMDID KVAFT GSTEV
GKLIK EAAGK SNLKR VTLEL GGKSP CIVLA DADLD NAVEF AHHGV FYHQG
QCCIA ASRIF VEESI YDEFV RRSVE RAKKY ILGNP LTPGV TQGPQ IDKEQ YDKIL
DLIES GKKEG AKLEC GGGPW GNKGY FVQPT VFSNV TDEMR IAKEE IFGPV
QQIMK FKSLD DVIKR ANNTF YGLSA GVFTK DIDKA ITISS ALQAG TVWVN
CYGVV SAQCP FGGFK MSGNG RELGE YGFHE YTEVK TVTVK ISQKN S
(SEQ ID NO: 4)

NCBI Reference Sequence for ALDH1A1: NM_000689
LOCUS NM_000689 2116 bp mRNA
DEFINITION Homo sapiens aldehyde dehydrogenase 1 family, member A1 (ALDH1A1), mRNA.
ACCESSION NM_000689

FIG. 13

```
   1 atcagctttg caagcaagta agggagcgga aaaggccggg aaaggccctg ccgcgagcac
  61 gctgccaaga gcccccagca gcagttcggc ttaggactcg ggttgcggcg ggtgtcacct
 121 tctcaggggc tagcaaggca gccagggccc aggcgtctga gtgaggggcg ggagaggagg
 181 cgaggcagaa agtggacctt ccagcggaaa ggccattttc cccaaggccg agcccaggga
 241 agtcccttcc tatagaattc aggcagggtg ggaggcaggg cgcgctcgtg cccctcagcc
 301 agctgcaggt gctctctgtc cccaggcgcc atgagcaaga tcagcgaggc cgtgaagcgc
 361 gcccgcgccg ccttcagctc gggcaggacc cgtccgctgc agttccggat ccagcagctg
 421 gaggcgctgc agcgcctgat ccaggagcag gagcaggagc tggtgggcgc gctggccgca
 481 gacctgcaca agaatgaatg gaacgcctac tatgaggagg tggtgtacgt cctagaggag
 541 atcgagtaca tgatccagaa gctccctgag tgggccgcgg atgagcccgt ggagaagacg
 601 ccccagactc agcaggacga gctctacatc cactcggagc cactgggcgt ggtcctcgtc
 661 attggcacct ggaactaccc cttcaacctc accatccagc ccatggtggg cgccatcgct
 721 gcagggaact cagtggtcct caagccctcg gagctgagtg agaacatggc gagcctgctg
 781 gctaccatca tcccccagta cctggacaag gatctgtacc cagtaatcaa tgggggtgtc
 841 cctgagacca cggagctgct caaggagagg ttcgaccata tcctgtacac gggcagcacg
 901 ggggtgggga agatcatcat gacggctgct gccaagcacc tgaccccctgt cacgctggag
 961 ctgggaggga agagtccctg ctacgtggac aagaactgtg acctggacgt ggcctgccga
1021 cgcatcgcct gggggaaatt catgaacagt ggccagacct gcgtggcccc tgactacatc
1081 ctctgtgacc cctcgatcca gaaccaaatt gtggagaagc tcaagaagtc actgaaagag
1141 ttctacgggg aagatgctaa gaaatcccgg gactatggaa gaatcattag tgcccggcac
1201 ttccagaggg tgatgggcct gattgagggc cagaaggtgg cttatggggg caccggggat
1261 gccgccactc gctacatagc ccccaccatc ctcacggacg tggaccccca gtccccggtg
1321 atgcaagagg agatcttcgg gcctgtgctg cccatcgtgt gcgtgcgcag cctggaggag
1381 gccatccagt tcatcaacca gcgtgagaag ccctggcccc tctacatgtt ctccagcaac
1441 gacaaggtga ttaagaagat gattgcagag acatccagtg gtggggtggc ggccaacgat
1501 gtcatcgtcc acatcacctt gcactctctg cccttcgggg gcgtggggaa cagcggcatg
1561 ggatcctacc atggcaagaa gagcttcgag actttctctc accgccgctc ttgcctggtg
1621 aggcctctga tgaatgatga aggcctgaag gtcagatacc ccccgagccc ggccaagatg
1681 acccagcact gaggagggt tgctccgcct ggcctggcca tactgtgtcc catcggagtg
1741 cggaccaccc tcactggctc tcctggccct gggagaatcg ctcctgcagc cccagcccag
1801 ccccactcct ctgctgacct gctgacctgt gcacacccca ctcccacatg ggcccaggcc
1861 tcaccattcc aagtctccac cccttttctag accaataaag agacgaatac aattttctaa
1921 ctcagcaaaa aaaaaaaaaa aaaa (SEQ ID NO: 5)
```

FIG. 14

MSKIS EAVKR ARAAF SSGRT RPLQF RIQQL EALQR LIQEQ EQELV GALAA
DLHKN EWNAY YEEVV YVLEE IEYMI QKLPE WAADE PVEKT PQTQQ DELYI
HSEPL GVVLV IGTWN YPFNL TIQPM VGAIA AGNSV VLKPS ELSEN MASLL ATIIP
QYLDK DLYPV INGGV PETTE LLKER FDHIL YTGST GVGKI IMTAA AKHLT
PVTLE LGGKS PCYVD KNCDL DVACR RIAWG KFMNS GQTCV APDYI LCDPS
IQNQI VEKLK KSLKE FYGED AKKSR DYGRI ISARH FQRVM GLIEG QKVAY
GGTGD AATRY IAPTI LTDVD PQSPV MQEEI FGPVL PIVCV RSLEE AIQFI NQREK
PLALY MFSSN DKVIK KMIAE TSSGG VAAND VIVHI TLHSL PFGGV GNSGM
GSYHG KKSFE TFSHR RSCLV RPLMN DEGLK VRYPP SPAKM TQH (SEQ ID NO: 6)

NCBI Reference Sequence for ALDH3A1: NM_001135168.1
LOCUS    NM_001135168       1944 bp   mRNA   linear
DEFINITION Homo sapiens aldehyde dehydrogenase 3 family, memberA1 (ALDH3A1),
      transcript variant 1, mRNA.
ACCESSION   NM_001135168

FIG. 15

HHHHHH(SEQ ID NO: 7)

FIG. 16

SEQUENCE LISTING

<160> NUMBER OF SEQ ID NOS: 7

<210> SEQ ID NO 1
<211> LENGTH: 1721
<212> TYPE: DNA
<213> ORGANISM: Homo sapiens

<400> SEQUENCE: 1

```
caccagcaca gcaaacccgc cgggatcaaa gtgtaccagt cggcagcatg gctacgaaat      60
gtgggaattg tggacccggc tactccaccc ctctggaggc catgaaagga cccagggaag     120
agatcgtcta cctgccctgc atttaccgaa acacaggcac tgaggcccca gattatctgg     180
ccactgtgga tgttgacccc aagtctcccc agtattgcca ggtcatccac cggctgccca     240
tgcccaacct gaaggacgag ctgcatcact caggatggaa cacctgcagc agctgcttcg     300
gtgatagcac caagtcgcgc accaagctgg tgctgcccag tctcatctcc tctcgcatct     360
atgtggtgga cgtgggctct gagccccggg ccccaaaagct gcacaaggtc attgagccca     420
aggacatcca tgccaagtgc gaactggcct ttctccacac cagccactgc ctggccagcg     480
gggaagtgat gatcagctcc ctgggagacg tcaagggcaa tggcaagggg ggttttgtgc     540
tgctggatgg ggagacgttc gaggtgaagg ggacatggga gagacctggg ggtgctgcac     600
cgttgggcta tgacttctgg taccagcctc gacacaatgt catgatcagc actgagtggg     660
cagctcccaa tgtcttacga gatggcttca accccgctga tgtggaggct ggactgtacg     720
ggagccactt atatgtatgg gactggcagc gccatgagat tgtgcagacc ctgtctctaa     780
aagatgggct tattccctttg gagatccgct tcctgcacaa cccagacgct gcccaaggct     840
ttgtgggctg cgcactcagc tccaccatcc agcgcttcta caagaacgag ggaggtacat     900
```

```
ggtcagtgga gaaggtgatc caggtgcccc ccaagaaagt gaagggctgg ctgctgcccg    960
aaatgccagg cctgatcacc gacatcctgc tctccctgga cgaccgcttc ctctacttca   1020
gcaactggct gcatggggac ctgaggcagt atgacatctc tgacccacag agaccccgcc   1080
tcacaggaca gctcttcctc ggaggcagca ttgttaaggg aggccctgtg caagtgctgg   1140
aggacgagga actaaagtcc cagccagagc ccctagtggt caagggaaaa cgggtggctg   1200
gaggccctca gatgatccag ctcagcctgg atgggaagcg cctctacatc accacgtcgc   1260
tgtacagtgc ctgggacaag cagttttacc ctgatctcat cagggaaggc tctgtgatgc   1320
tgcaggttga tgtagacaca gtaaaaggag ggctgaagtt gaaccccaac ttcctggtgg   1380
acttcgggaa ggagcccctt ggcccagccc ttgcccatga gctccgctac cctgggggcg   1440
attgtagctc tgacatctgg atttgaactc caccctcatc acccacactc cctattttgg   1500
gccctcactt ccttggggac ctggcttcat tctgctctct cttggcaccc gaccccttggc  1560
agcatgtacc acacagccaa gctgagactg tggcaatgtg ttgagtcata tacatttact   1620
gaccactgtt gcttgttgct cactgtgctg cttttccatg agctcttgga ggcaccaaga   1680
aataaactcg taaccctgtc cttcaaaaaa aaaaaaaaa a                        1721
```

<210> SEQ ID NO 2
<211> LENGTH: 472
<212> TYPE: PRT
<213> ORGANISM: Homo sapiens

<400> SEQUENCE: 2

```
Met Ala Thr Lys Cys Gly Asn Cys Gly Pro Gly Tyr Ser Thr Pro Leu
1               5                   10                  15

Glu Ala Met Lys Gly Pro Arg Glu Ile Val Tyr Leu Pro Cys Ile
            20                  25                  30

Tyr Arg Asn Thr Gly Thr Glu Ala Pro Asp Tyr Leu Ala Thr Val Asp
        35                  40                  45

Val Asp Pro Lys Ser Pro Gln Tyr Cys Gln Val Ile His Arg Leu Pro
    50                  55                  60

Met Pro Asn Leu Lys Asp Glu Leu His His Ser Gly Trp Asn Thr Cys
65                  70                  75                  80

Ser Ser Cys Phe Gly Asp Ser Thr Lys Ser Arg Thr Lys Leu Val Leu
                85                  90                  95

Pro Ser Leu Ile Ser Ser Arg Ile Tyr Val Val Asp Val Gly Ser Glu
            100                 105                 110

Pro Arg Ala Pro Lys Leu His Lys Val Ile Glu Pro Lys Asp Ile His
        115                 120                 125

Ala Lys Cys Glu Leu Ala Phe Leu His Thr Ser His Cys Leu Ala Ser
    130                 135                 140

Gly Glu Val Met Ile Ser Ser Leu Gly Asp Val Lys Gly Asn Gly Lys
145                 150                 155                 160

Gly Gly Phe Val Leu Leu Asp Gly Glu Thr Phe Glu Val Lys Gly Thr
                165                 170                 175

Trp Glu Arg Pro Gly Gly Ala Ala Pro Leu Gly Tyr Asp Phe Trp Tyr
            180                 185                 190

Gln Pro Arg His Asn Val Met Ile Ser Thr Glu Trp Ala Ala Pro Asn
        195                 200                 205

Val Leu Arg Asp Gly Phe Asn Pro Ala Asp Val Glu Ala Gly Leu Tyr
    210                 215                 220

Gly Ser His Leu Tyr Val Trp Asp Trp Gln Arg His Glu Ile Val Gln
225                 230                 235                 240
```

```
Thr Leu Ser Leu Lys Asp Gly Leu Ile Pro Leu Glu Ile Arg Phe Leu
            245                 250                 255

His Asn Pro Asp Ala Ala Gln Gly Phe Val Gly Cys Ala Leu Ser Ser
        260                 265                 270

Thr Ile Gln Arg Phe Tyr Lys Asn Glu Gly Gly Thr Trp Ser Val Glu
    275                 280                 285

Lys Val Ile Gln Val Pro Pro Lys Val Lys Gly Trp Leu Pro
290                 295                 300

Glu Met Pro Gly Leu Ile Thr Asp Ile Leu Ser Leu Asp Asp Arg
305                 310                 315                 320

Phe Leu Tyr Phe Ser Asn Trp Leu His Gly Asp Leu Arg Gln Tyr Asp
                325                 330                 335

Ile Ser Asp Pro Gln Arg Pro Arg Leu Thr Gly Gln Leu Phe Leu Gly
            340                 345                 350

Gly Ser Ile Val Lys Gly Gly Pro Val Gln Val Leu Glu Asp Glu Glu
        355                 360                 365

Leu Lys Ser Gln Pro Glu Pro Leu Val Val Lys Gly Lys Arg Val Ala
    370                 375                 380

Gly Gly Pro Gln Met Ile Gln Leu Ser Leu Asp Gly Lys Arg Leu Tyr
385                 390                 395                 400

Ile Thr Thr Ser Leu Tyr Ser Ala Trp Asp Lys Gln Phe Tyr Pro Asp
                405                 410                 415

Leu Ile Arg Glu Gly Ser Val Met Leu Gln Val Asp Val Asp Thr Val
            420                 425                 430

Lys Gly Gly Leu Lys Leu Asn Pro Asn Phe Leu Val Asp Phe Gly Lys
        435                 440                 445

Glu Pro Leu Gly Pro Ala Leu Ala His Glu Leu Arg Tyr Pro Gly Gly
    450                 455                 460

Asp Cys Ser Ser Asp Ile Trp Ile
465                 470

<210> SEQ ID NO 3
<211> LENGTH: 2116
<212> TYPE: DNA
<213> ORGANISM: Homo sapiens

<400> SEQUENCE: 3 atcagaaacca aattgctgag ccagtcacct gtgttccagg agccgaatca gaaatgtcat      60
cctcaggcac gccagactta cctgtcctac tcaccgattt gaagattcaa tatactaaga     120
tcttcataaa caatgaatgg catgattcag tgagtggcaa gaaatttcct gtctttaatc     180
ctgcaactga ggaggagctc tgccaggtag aagaaggaga taaggaggat gttgacaagg     240
cagtgaaggc cgcaagacag gcttttcaga ttggatcccc gtggcgtact atggatgctt     300
ccgagagggg gcgactatta tacaagttgg ctgatttaat cgaaagagat cgtctgctgc     360
tggcgacaat ggagtcaatg aatggtggaa aactctattc caatgcatat ctgaatgatt     420
tagcaggctg catcaaaaca ttgcgctact gtgcaggttg gctgacaag atccagggcc      480 gtacaatacc aattgatgga aattttttta catatacaag acatgaacct attggtgtat     540
gtggccaaat cattccttgg aatttcccgt tggttatgct catttggaag atagggcctg     600
cactgagctg tggaaacaca gtggttgtca accagcagag gcaaactcct ctcactgctc     660
tccacgtggc atctttaata aaagaggcag ggtttcctcc tgagtagtg aatattgttc      720 ctggttatgg gcctacagca ggggcagcca tttcttctca catggatata gacaaagtag     780
```

```
ccttcacagg atcaacagag gttggcaagt tgatcaaaga agctgccggg aaaagcaatc   840
tgaagagggt gaccctggag cttggaggaa agagcccttg cattgtgtta gctgatgccg   900
acttggacaa tgctgttgaa tttgcacacc atggggtatt ctaccaccag gccagtgtt    960 gtatagccgc atccaggatt tttgtggaag aatcaattta tgatgagttt gttcgaagga  1020
gtgttgagcg ggctaagaag tatatccttg aaatcctct gaccccagga gtcactcaag   1080
gccctcagat tgacaaggaa caatatgata aatacttga cctcattgag agtgggaaga   1140 aagaagggc caaactggaa tgtggaggag gcccgtgggg aataaaggc tactttgtcc    1200 agcccacagt gttctctaat gttacagatg agatgcgcat tgccaaagag gagatttttg  1260
gaccagtgca gcaaatcatg aagtttaaat ctttagatga cgtgatcaaa agagcaaaca  1320
atactttcta tggcttatca gcaggagtgt ttaccaaaga cattgataaa gccataacaa  1380
tctcctctgc tctgcaggca ggaacagtgt gggtgaattg ctatggcgtg gtaagtgccc  1440 agtgccccctt tggtggattc aagatgtctg gaaatggaag agaactggga gagtacggtt  1500
tccatgaata tacagaggtc aaaacagtca cagtgaaaat ctctcagaag aactcataaa   1560
gaaaatacaa gagtggagag aagctcttca atagctaagc atctccttac agtcactaat   1620
atagtagatt ttaaagacaa aattttctt tcttgattt ttttaaacat aagctaaatc     1680
atattagtat taatactacc catagaaaac ttgacatgta gcttcttctg aaagaattat   1740
ttgccttctg aaatgtgacc cccaagtcct atcctaaata aaaaaagaca aattcggatg   1800
tatgatctct ctagctttgt catagttatg tgattttcct ttgtagctac ttttgcagga   1860
taataatttt atagaaaagg aacagttgca tttagcttct ttcccttagt gactcttgaa   1920
gtacttaaca tacacgttaa ctgcagagta aattgctctg ttcccagtag ttataaagtc   1980
cttggactgt tttgaaaagt ttcctaggat gtcatgtctg cttgtcaaaa gaaataatcc   2040
ctgtaatatt tagctgtaaa ctgaatataa agcttaataa aaacaacctt gcatgaaaaa   2100
aaaaaaaaaa aaaaaa                                                  2116
```

<210> SEQ ID NO 4
<211> LENGTH: 501
<212> TYPE: PRT
<213> ORGANISM: Homo sapiens

<400> SEQUENCE: 4

```
Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Asn Asp Leu Ala Gly Cys Ile Lys
        115                 120                 125

Thr Leu Arg Tyr Cys Ala Gly Trp Ala Asp Lys Ile Gln Gly Arg Thr
    130                 135                 140
```

```
Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
                165                 170                 175

Ile Trp Lys Ile Gly Pro Ala Leu Ser Cys Gly Asn Thr Val Val Val
            180                 185                 190

Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
    210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
        275                 280                 285

Glu Phe Ala His His Gly Val Phe Tyr His Gln Gly Gln Cys Cys Ile
    290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
            340                 345                 350

Lys Ile Leu Asp Leu Ile Glu Ser Gly Lys Lys Glu Gly Ala Lys Leu
        355                 360                 365

Glu Cys Gly Gly Gly Pro Trp Gly Asn Lys Gly Tyr Phe Val Gln Pro
    370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
        435                 440                 445

Ala Gly Thr Val Trp Val Asn Cys Tyr Gly Val Val Ser Ala Gln Cys
    450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500

<210> SEQ ID NO 5
<211> LENGTH: 1944
<212> TYPE: DNA
<213> ORGANISM: Homo sapiens

<400> SEQUENCE: 5
atcagctttg caagcaagta agggagcgga aaaggccggg aaaggccctg ccgcgagcac      60
```

```
gctgccaaga gcccccagca gcagttcggc ttaggactcg ggttgcggcg ggtgtcacct    120
tctcagggggc tagcaaggca gccagggccc aggcgtctga gtgaggggcg ggagaggagg    180
cgaggcagaa agtggacctt ccagcggaaa ggccattttc cccaaggccg agcccaggga    240
agtcccttcc tatagaattc aggcagggtg ggaggcaggg cgcgctcgtg cccctcagcc    300
agctgcaggt gctctctgtc cccaggcgcc atgagcaaga tcagcgaggc cgtgaagcgc    360
gcccgcgccg ccttcagctc gggcaggacc cgtccgctgc agttccggat ccagcagctg    420
gaggcgctgc agcgcctgat ccaggagcag gagcaggagc tggtgggcgc gctggccgca    480
gacctgcaca gaatgaatg aacgcctac tatgaggagg tggtgtacgt cctagaggag    540
atcgagtaca tgatccagaa gctccctgag tgggccgcgg atgagcccgt ggagaagacg    600
ccccagactc agcaggacga gctctacatc cactcggagc cactgggcgt ggtcctcgtc    660
attggcacct ggaactaccc cttcaacctc accatccagc ccatggtggg cgccatcgct    720
gcagggaact cagtggtcct caagccctcg gagctgagtg agaacatggc gagcctgctg    780
gctaccatca tcccccagta cctggacaag gatctgtacc cagtaatcaa tgggggtgtc    840
cctgagacca cggagctgct caaggagagg ttcgaccata tcctgtacac gggcagcacg    900
ggggtgggga agatcatcat gacggctgct gccaagcacc tgacccctgt cacgctggag    960
ctgggaggga agagtccctg ctacgtggac aagaactgtg acctggacgt ggcctgccga   1020
cgcatcgcct gggggaaatt catgaacagt ggccagacct gcgtggcccc tgactacatc   1080
ctctgtgacc cctcgatcca gaaccaaatt gtggagaagc tcaagaagtc actgaaagag   1140
ttctacgggg aagatgctaa gaaatcccgg gactatggaa gaatcattag tgcccggcac   1200
ttccagaggg tgatgggcct gattgagggc cagaaggtgg cttatggggg caccggggat   1260
gccgccactc gctacatagc ccccaccatc ctcacggacg tggaccccca gtccccggtg   1320
atgcaagagg agatcttcgg gcctgtgctg cccatcgtgt gcgtgcgcag cctggaggag   1380
gccatccagt tcatcaacca gcgtgagaag cccctggccc tctacatgtt ctccagcaac   1440
gacaaggtga ttaagaagat gattgcagag acatccagtg gtggggtggc ggccaacgat   1500
gtcatcgtcc acatcaccct tgcactctctg cccttcgggg gcgtggggaa cagcggcatg   1560
ggatcctacc atggcaagaa gagcttcgag actttctctc accgccgctc ttgcctggtg   1620
aggcctctga tgaatgatga aggcctgaag gtcagatacc ccccgagccc ggccaagatg   1680
acccagcact gaggaggggt tgctccgcct ggcctggcca tactgtgtcc catcggagtg   1740
cggaccaccc tcactggctc tcctggcccct gggagaatcg ctcctgcagc ccagcccag   1800
ccccactcct ctgctgacct gctgacctgt gcacacccca ctcccacatg ggcccaggcc   1860
tcaccattcc aagtctccac cccttctag accaataaag agacgaatac aattttctaa   1920
ctcagcaaaa aaaaaaaaaa aaaa                                          1944
```

<210> SEQ ID NO 6
<211> LENGTH: 453
<212> TYPE: PRT
<213> ORGANISM: Homo sapiens

<400> SEQUENCE: 6

Met Ser Lys Ile Ser Glu Ala Val Lys Arg Ala Arg Ala Ala Phe Ser
1               5                   10                  15

Ser Gly Arg Thr Arg Pro Leu Gln Phe Arg Ile Gln Gln Leu Glu Ala
            20                  25                  30

Leu Gln Arg Leu Ile Gln Glu Gln Glu Gln Glu Leu Val Gly Ala Leu
        35                  40                  45

```
Ala Ala Asp Leu His Lys Asn Glu Trp Asn Ala Tyr Tyr Glu Glu Val
 50                  55                  60

Val Tyr Val Leu Glu Glu Ile Glu Tyr Met Ile Gln Lys Leu Pro Glu
 65                  70                  75                  80

Trp Ala Ala Asp Glu Pro Val Glu Lys Thr Pro Gln Thr Gln Gln Asp
                 85                  90                  95

Glu Leu Tyr Ile His Ser Glu Pro Leu Gly Val Val Leu Val Ile Gly
            100                 105                 110

Thr Trp Asn Tyr Pro Phe Asn Leu Thr Ile Gln Pro Met Val Gly Ala
        115                 120                 125

Ile Ala Ala Gly Asn Ser Val Val Leu Lys Pro Ser Glu Leu Ser Glu
    130                 135                 140

Asn Met Ala Ser Leu Leu Ala Thr Ile Ile Pro Gln Tyr Leu Asp Lys
145                 150                 155                 160

Asp Leu Tyr Pro Val Ile Asn Gly Gly Val Pro Glu Thr Thr Glu Leu
                165                 170                 175

Leu Lys Glu Arg Phe Asp His Ile Leu Tyr Thr Gly Ser Thr Gly Val
            180                 185                 190

Gly Lys Ile Ile Met Thr Ala Ala Ala Lys His Leu Thr Pro Val Thr
        195                 200                 205

Leu Glu Leu Gly Gly Lys Ser Pro Cys Tyr Val Asp Lys Asn Cys Asp
210                 215                 220

Leu Asp Val Ala Cys Arg Arg Ile Ala Trp Gly Lys Phe Met Asn Ser
225                 230                 235                 240

Gly Gln Thr Cys Val Ala Pro Asp Tyr Ile Leu Cys Asp Pro Ser Ile
                245                 250                 255

Gln Asn Gln Ile Val Glu Lys Leu Lys Lys Ser Leu Lys Glu Phe Tyr
            260                 265                 270

Gly Glu Asp Ala Lys Lys Ser Arg Asp Tyr Gly Arg Ile Ile Ser Ala
        275                 280                 285

Arg His Phe Gln Arg Val Met Gly Leu Ile Glu Gly Gln Lys Val Ala
    290                 295                 300

Tyr Gly Gly Thr Gly Asp Ala Ala Thr Arg Tyr Ile Ala Pro Thr Ile
305                 310                 315                 320

Leu Thr Asp Val Asp Pro Gln Ser Pro Val Met Gln Glu Glu Ile Phe
                325                 330                 335

Gly Pro Val Leu Pro Ile Val Cys Val Arg Ser Leu Glu Glu Ala Ile
            340                 345                 350

Gln Phe Ile Asn Gln Arg Glu Lys Pro Leu Ala Leu Tyr Met Phe Ser
        355                 360                 365

Ser Asn Asp Lys Val Ile Lys Lys Met Ile Ala Glu Thr Ser Ser Gly
370                 375                 380

Gly Val Ala Ala Asn Asp Val Ile Val His Ile Thr Leu His Ser Leu
385                 390                 395                 400

Pro Phe Gly Gly Val Gly Asn Ser Gly Met Gly Ser Tyr His Gly Lys
                405                 410                 415

Lys Ser Phe Glu Thr Phe Ser His Arg Arg Ser Cys Leu Val Arg Pro
            420                 425                 430

Leu Met Asn Asp Glu Gly Leu Lys Val Arg Tyr Pro Pro Ser Pro Ala
        435                 440                 445

Lys Met Thr Gln His
450
```

```
<210> SEQ ID NO 7
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 7

His His His His His His
1               5
```

DIAGNOSTIC TESTS FOR ABNORMAL OVARIAN CONDITIONS

CROSS REFERENCE TO RELATED APPLICATIONS

This application is a U.S. nationalization under 35 U.S.C. §371 of International Application No. PCT/US2010/049245, filed Sep. 17, 2010, which claims priority to U.S. provisional application No. 61/243,247, filed Sep. 17, 2009. The disclosures set forth in the referenced applications are incorporated herein by reference in their entireties.

STATEMENT REGARDING FEDERALLY SPONSORED RESEARCH

The present invention was made in part with U.S. Government support under grant number 1RO1 AI 055060-01 from the National Institutes of Health. The U.S. Government may have certain rights to this invention.

BACKGROUND OF THE DISCLOSURE

Abnormal ovarian conditions include cancer, autoimmunity, and premature ovarian failure. Infertility is one of the clinical manifestations.

Ovarian cancer is the leading cause of gynecologic cancer death in the developed world largely because there is no effective screening method, and symptoms occur late in the progression of the disease. New biomarkers are needed if screening is to have an impact on outcomes of females with ovarian cancer and/or ovarian autoimmunity. Because ovarian cells cannot be readily obtained from the female genital tract, a screening method based on the analysis of serum biomarkers is highly desired.

Strong evidence exists for an autoimmune disease of the ovary, but no corresponding, standardized commercial test is available for its clinical diagnosis. The disease is associated with specific anti-ovarian antibodies. Ovarian autoimmune disease occurs in but is not limited to women with infertility and in women with premature menopause. Not all women attempt to have children. Infertility is defined as the inability to conceive. Premature menopause (Premature Ovarian Failure, POF) is defined as cessation of menstruation before age 40. Based on extensive epidemiologic studies women who have never given birth are at are at high risk for ovarian cancer and would also benefit from antibody screening.

Ovarian function is assessed by evaluation of menstrual cycle patterns, cycle length, and measurement of early follicular phase FSH and estradiol. Early changes associated with ovarian failure, such as infertility or minor elevations of FSH (above 10 mIU/ml) may be subtle. Later changes may include more obvious disturbances, such as menstrual cycle changes, and elevations of FSH (above 40 mIU/ml). Although these changes are normal as a woman approaches menopause around age 50, the same changes in young women may signal a pathological process. However, endocrine tests do not differentiate between endocrine and autoimmune etiologies for ovarian dysfunction. Current hormone treatment of ovarian dysfunction may be less successful in the face of ovarian autoimmune disease.

Previously, the only method available for ovarian autoantibody detection was immunohistochemistry, and a prototype immunoassay test. Unfortunately immunohistochemical methods are subjective, labor intensive, qualitative, and—particularly with the ovary—are subject to significant variations in antigen content between tissue sections. The prototype ovarian antibody test was based on use of a microsomal fraction of the ovary in an ELISA format. The specific antigens reacting with patient sera were not identified in the prototype test. An improvement over this nonspecific ovarian antibody test is the test described in U.S. Pat. No. 6,458,550 and incorporated herein by reference. This assay was developed to test for autoimmunity by using autoantibodies to CYP17.

Antibodies to CYP17 are more common in patients with concomitant endocrine autoimmunity involving the adrenal (polyendocrine autoimmunity type 1 and 2) and do not detect all patients with ovarian autoimmunity.

Although it is less common than other gynecologic cancers, ovarian cancer mortality represents 2.5% of cancer deaths in the United States. This reflects a lack of early detection methods, because less than 25% of ovarian tumors are detected at Stage I. The five-year survival of patients with stage I/II ovarian tumors (80-90%) is dramatically higher than patients who are diagnosed with stage IV tumors (less than 30%). Improved survival rates result from early detection for prostate cancer (PSA test), breast cancer (mammography) and cervical cancer (PAP smear), thus earlier detection of ovarian tumors will significantly increase survival.

Despite reports describing tumor markers, there is currently no reliable diagnostic or screening test for ovarian cancer. Ovarian cancer does not usually cause symptoms at first. Many women have some symptoms, such as gas or pain or swelling in the abdomen, in the 6 to 12 months before ovarian cancer is found. Other symptoms are diarrhea or constipation, or an upset stomach. These symptoms are general and are more likely to be attributed to other causes. Usually, the cancer has spread by the time it is found. Currently, if ovarian cancer is suspected due to a pelvic mass during a pelvic exam, exploratory surgery is performed.

There is a plethora of putative protein markers reported for ovarian cancer, CA-125 being the most well known. CA-125, however, has poor specificity and predictive value for ovarian cancer detection, since it increases in endometriosis and during the normal menstrual cycle, and in the presence of other cancers. Among many non-specific markers identified in association with ovarian cancer, two have been described that appear to be relatively specific for ovarian cancer; mesothelin and HE4. However, this association was demonstrated only for relatively advanced stage ovarian cancer, making these markers less useful for predicting the onset of ovarian cancer at an early stage.

The biological activity of selenium (Se) has been studied for over 40 years and is now recognized as an essential trace element in eukaryotes and as a potent anticarcinogenic agent. Dietary Se affords protection against both the initiation and promotion of carcinogenesis, and there is increasing epidemiological evidence to support its anticarcinogenic role in humans. Se-binding proteins from various species including human have been identified and characterized. Some of them belong to a family of highly homologous cytosolic proteins with similar molecular weights (ca. 54-58 kDa) and overlapping tissue distributions in the kidney, liver, lung, gastrointestinal tract, and male and female endocrine glands. Se-binding proteins have been implicated in cellular growth control and protection from carcinogenesis and cancer.

Epidemiologic data indicates that women with infertility have a higher risk for ovarian and other cancers than women in the general population or women without infertility. There is no test to determine which patients have a higher risk for ovarian cancer or have very early tumors and would benefit from closer monitoring in order to detect ovarian cancer early when survival probability is highest.

SUMMARY OF THE DISCLOSURE

As a result of immunoproteomic discovery methods using autoantibodies, several proteins including SELENBP1 and ALDH1A1 were identified in infertility patient sera. Methods of diagnosing ovarian autoimmunity and ovarian cancer (OvCa), include the detection of specific autoantibodies. In addition to screening for ovarian cancer, detection of these autoantibodies differentiates etiologies of infertility and premature ovarian failure. A panel of specific autoantibodies is also suitable to screen for ovarian disorders. A panel of autoantibodies in combination with personal, medical and epidemiologic risk factors will discriminate women with high risk and low risk for ovarian cancer.

An immunoassay is described that measures the presence and/or concentration of autoantibodies e.g., such as an anti-SELENBP1, anti-ALDH and other autoantibodies in a biological sample taken from a mammal, wherein the immunoassay includes the steps of: (a) contacting the biological sample with an antigen specific for the antibodies, the contacting being under conditions sufficient to permit antibodies, if present in the sample, to bind to the antigen and form an autoantibody complex e.g., antigen-anti-SELENBP1. In addition to tests for individual specific autoantibodies, a panel of a plurality of OvCa biochemical markers are assembled into a multiplex assay (e.g., 10 examples could include mesothelin, HE4, CA125, MUC1, p53, ALDH1, ALDH3, SELENBP1, enolase and vimentin). To determine if panels are suitable, results in patients with known autoimmune disorders are compared to healthy controls, to determine what antibodies differentiate the groups.

Detection of autoantibodies is combined with assessment of risk factors to construct a stratification method to identify those at high risk for close monitoring and follow up testing. This will change current clinical practice and dramatically reduce mortality and the healthcare cost of OvCa. Furthermore, methods are provided for diagnosing ovarian autoimmunity associated with unexplained infertility or idiopathic POF that occurs in the absence of polyglandular disease. Ovarian autoimmunity is detectable before the onset of ovarian dysfunction. Thus, those individuals are identified who would benefit from therapy to maintain, as well as restore, ovarian function. For example, individuals with ovarian autoimmunity may be counseled to bear children before it becomes difficult or impossible due to loss of ovarian function.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

FIG. 1 shows a summary of antibody detection by ELISA.

FIG. 10 is SEQ ID NO: 1.
FIG. 11 is SEQ ID NO: 2.
FIG. 12 is SEQ ID NO: 3.
FIG. 13 is SEQ ID NO: 4.
FIG. 14 is SEQ ID NO: 5.
FIG. 15 is SEQ ID NO: 6.
FIG. 16 is SEQ ID NO: 7.

DETAILED DESCRIPTION OF THE DISCLOSURE

Figure 2:
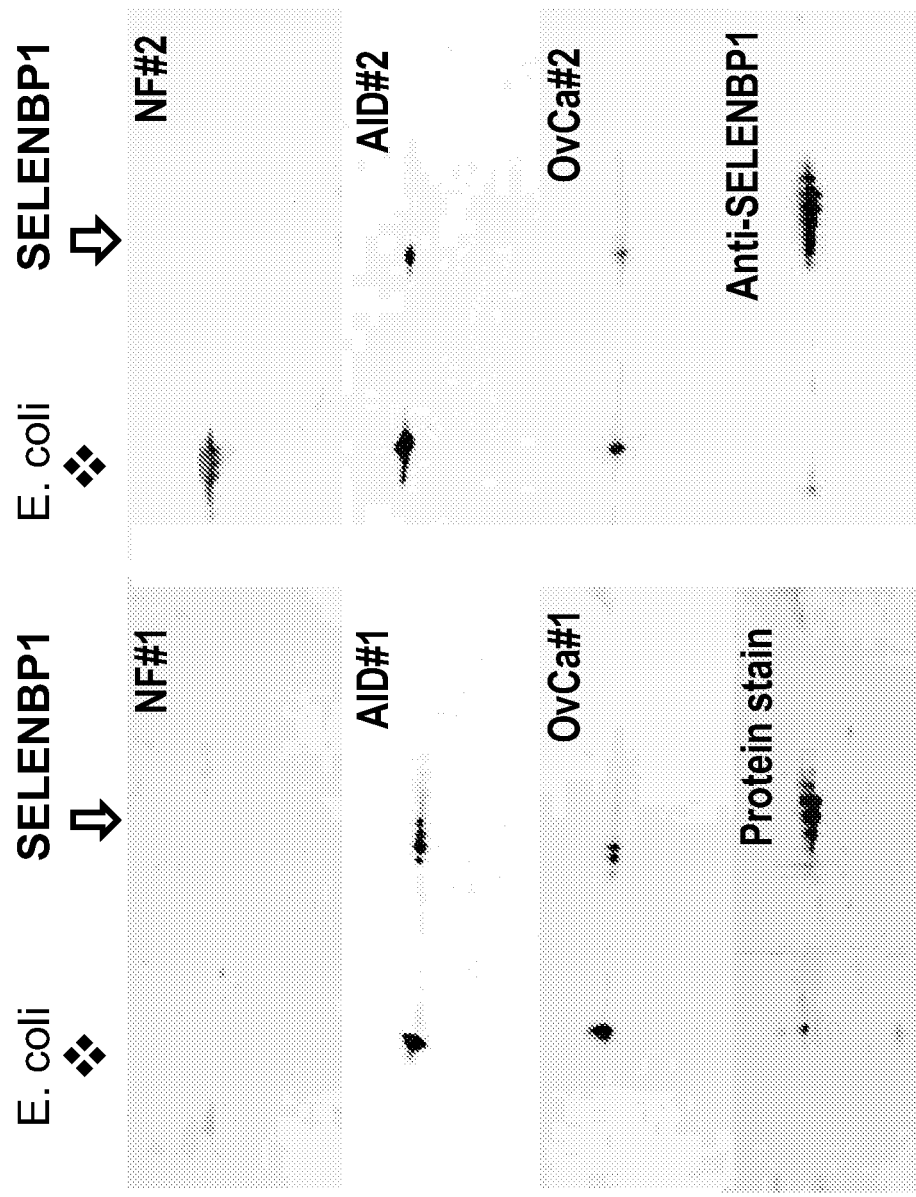
FIG. 2 shows a 2D Western blot using recombinant SELENBP1 testing sera from women with or without ovarian autoimmunity.

Methods and compositions, which may be in a kit for, are described for use in diagnosing ovarian autoimmunity and ovarian cancer. A biological basis for autoantibodies as predictors of OvCa is supported by results in an animal model of spontaneous OvCa (the laying hen); hens with reduced ovarian function (reduced egg laying) and ovarian antibodies but no detectable tumor histology, developed tumor angiogenesis and malignant ovarian tumors, while antibody negative hens did not develop OvCa. Anti-ovarian antigen positive sera were used to identify antigens using immunoproteomics. Some of the key proteins identified by mass spectrometry included aldehyde dehydrogenase 1 (ALDH1A1), protein disulfide-isomerase A3 (PDIA3), vimentin (VIME), α-enolase (ENOA), glyceraldehyde-3-phosphate dehydrogenase (G3PD or GAPDH) and Selenium Binding Protein 1 (SELENBP1). Interestingly, SELENBP1 is a novel protein that is expressed in surface epithelial cells of normal ovary and is downregulated in OvCa as well as other epithelial cancers. Furthermore, methods and kits are provided for diagnosing ovarian autoimmunity associated with unexplained infertility or idiopathic premature ovarian failure (POF) that occurs in the absence of polyglandular disease. Methods and composition described herein are used to detect ovarian autoimmunity before the onset of ovarian dysfunction. Thus, those individuals are identified who would benefit from therapy to maintain, as well as restore, ovarian function.

Antibodies are excellent markers for autoimmune diseases because they are (a) specific; (b) able to detect low levels of antigen; and (c) biochemically stable. Furthermore, "anti-tumor antibody (ATA)" responses tend to be unique to cancer patients, despite the fact that most of the relevant antigens are also found in normal tissue with a few exceptions such as the cancer/testis antigens. Since protein expression among tumors is heterogeneous, few single antibody-antigen reactions identify more than 20-30% of patients. While the antibodies appear to be a unique component associated with tumors, multiple antigens are needed to detect tumors across a group of patients because the antigen specificity of anti-tumor antibodies reflects the individual array of proteins expressed in each patient's tumor. (e.g., SELENBP1, ALDH1, ALDH3, enolase and vimentin).

An embodiment of an antibody screening panel disclosed contemplates a paratope-containing molecule such as an antibody that specifically binds to (immunoreacts with) human SELENBP1, human ALDH, human ALDH1A1 or human ALDH3A1 and particularly binds to an epitope that is present on the molecule.

FIG. 1 shows a summary of antibody detection using ELISA. The percent of sera positive for one or more antibodies in Infertility and Ovarian Cancer (OvCa) in comparison to benign conditions with normal sera used to determine positive values. Antibody positive sera (1:100) were detected by direct ELISA using 8 antigens (See FIG. 4). Positive values were those 2 SD above the mean control (normal sera) optical density ($p<0.05$).

In FIG. 2 Sera from two women with ovarian autoimmunity (AID), and two with ovarian cancer (OvCa), but not two normal females (NF) reacted with SBP1 as determined by 2D Western blot using recombinant SBP1. Identical results were obtained with 25 patient sera and 15 normal sera.

For the 2D Western blots, ten micrograms of total protein were passively rehydrated into an IPG strip (Bio-Rad, 3-10NL) and isoelectric focusing was done according to the manufacturers suggested protocol. The IPG strip was applied to a 10% Tris-HCL SDS-PAGE gel (Bio-Rad, 161-1390) and electrophoresed. Gels were transferred to nitrocellulose membranes, and after blocking (1× Blocking buffer containing 0.05% Tween; Sigma-Aldrich) (1 hour, 22° C.), membranes were probed with sera (1:500; 16 hours, 4° C.). After three washes with TBST (TBS containing 0.05% Tween), membranes were incubated with goat anti human immunoglobulin (IgG/M/A) conjugated with horseradish peroxidase (1:10,000) as secondary antibody (1 hour, 22° C.). Antibody reaction was visualized with an enhanced chemiluminescence reagent (SuperSignal West Dura extended duration substrate; Thermo Scientific) and images were captured with a Chemidoc imaging system (Bio-Rad).

Figure 3:
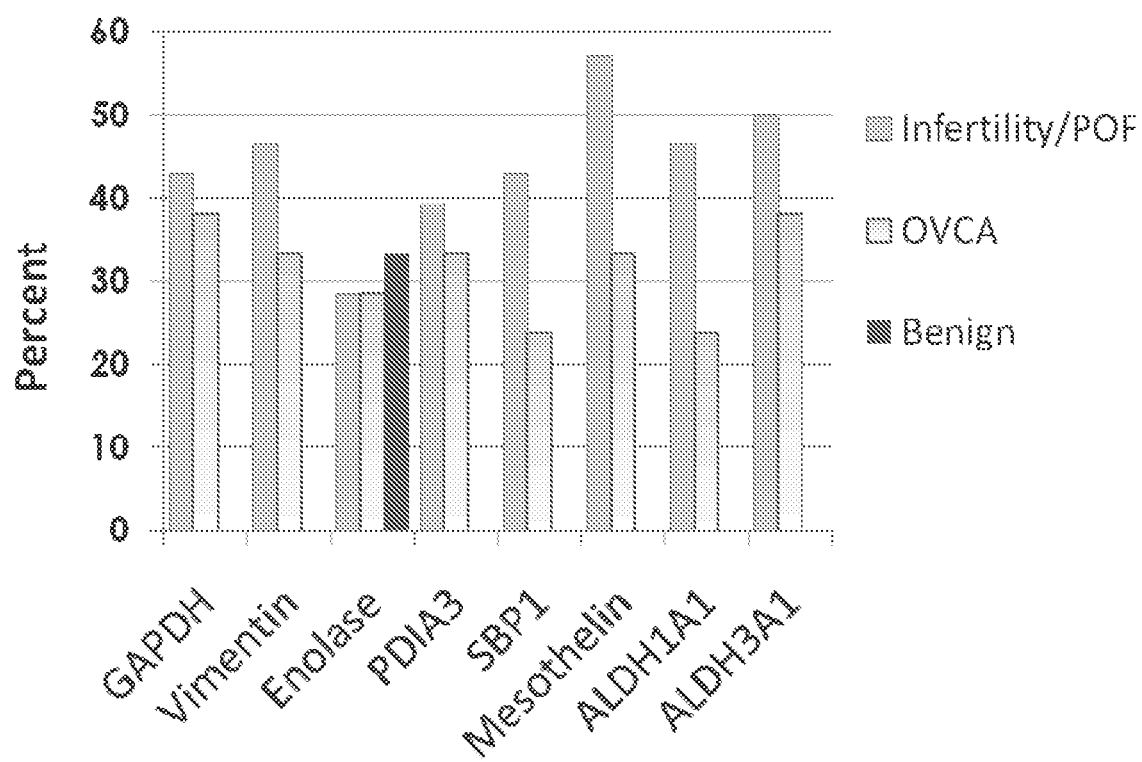
FIG. 3 shows percent of sera positive for antibodies to 8 individual antigens in samples from subjects with Infertility, ovarian cancer (OvCa) or benign gynecology & tumor controls (benign) detected by ELISA.

In FIG. 3 the percent of sera positive for antibodies to 8 individual antigens in sera of patients with either Infertility or POF (n=28), Ovarian cancer (OvCa) (n=21) or benign tumors (Benign) (n=9) was detected by direct ELISA. The results show autoantibodies to similar antigens in patents with infertility and ovarian cancer, but not in benign controls. Benign controls only reacted with enolase at a similar frequency as infertility and OvCa sera.

For the immunoassay, ELISA plates were coated with purified recombinant protein (50 ng/well in 10 mM phosphate buffer, 30 mM NaCl, 1 mM MgC12, pH7.4; 16 hours; 4° C.), except mesothelin and GAPDH which were purified from human tissue. Plates were blocked with 200u1 of 5% BSA in ELISA wash buffer for 2 hours. After three washes, sera were added (1:100 diluted in 1% BSA ELISA wash buffer) in duplicate wells. Plates were incubated (2 hours) and washed three times. Anti human immunoglobulin conjugated to alkaline phosphatase (100 µl; 1:10,000 in 1% BSA ELISA wash buffer) were added as secondary antibody and incubated (1 hour). After 2 washes with ELISA buffer and three washes in water (Baxter), AP substrate (Sigma) was added and the OD read at 30 minutes. The results for duplicate wells were averaged. Positive values were identified if the average OD value was greater than the control (normal females, n=6) mean+2 SD.

Figure 4:
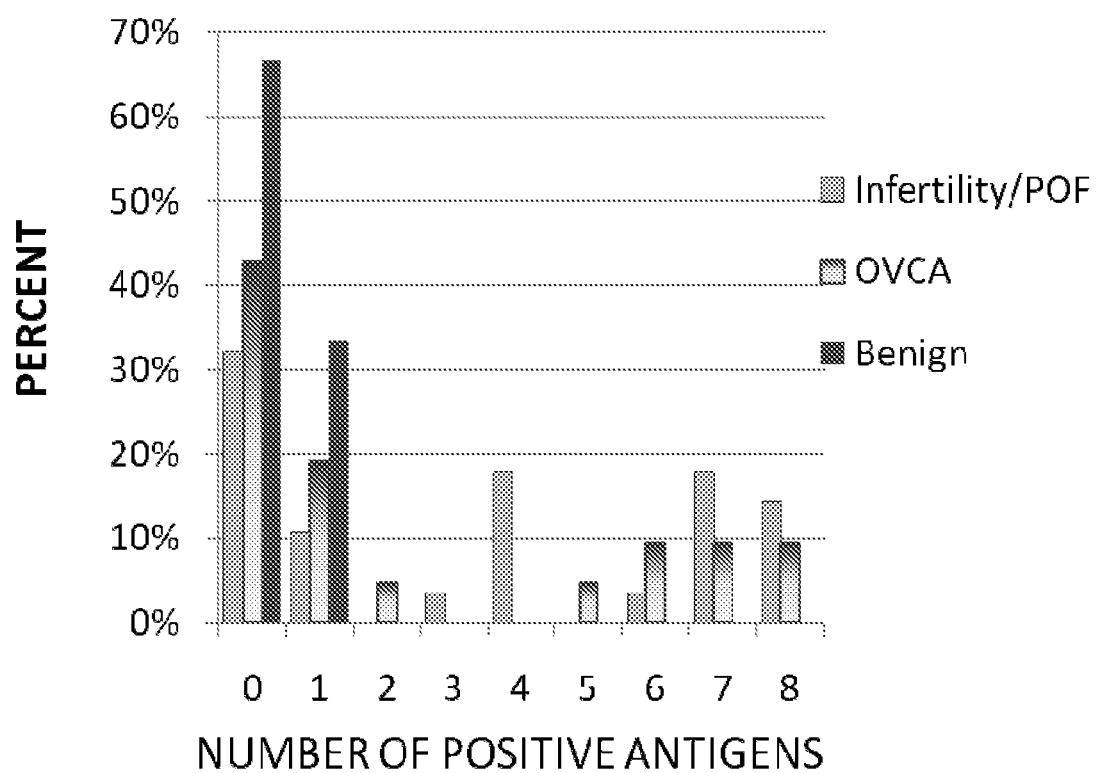
FIG. 4 shows a summary of the frequency of antigen reactions in samples from subjects with Infertility, Ovarian cancer (OvCa) and benign gynecology or tumor controls detected by ELISA.
Figure 5:
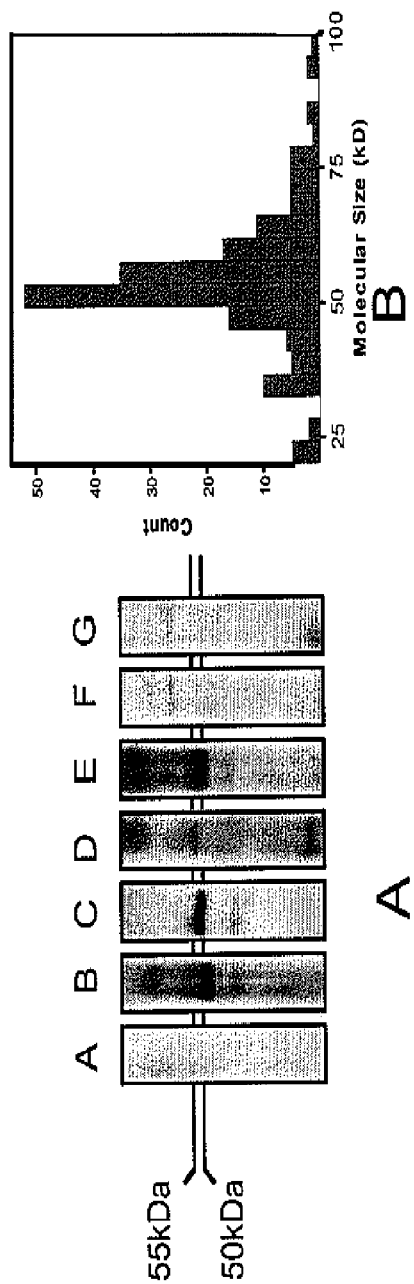
FIG. 5 (A & B) (A) One-dimensional Western blot showing examples of immunoreactions against human ovarian proteins (250 µg/gel). A negative control serum (Panel A) and examples of positive sera (Panels B-G) are shown. (B) Frequency distribution of the molecular size of immunoreactive bands among positive sera from women with unexplained infertility (n=50/74). The most frequent bands were at 50-56 kDa. The data shown were detected using rat ovarian proteins. The frequency distribution was similar for human proteins.
Figure 6:
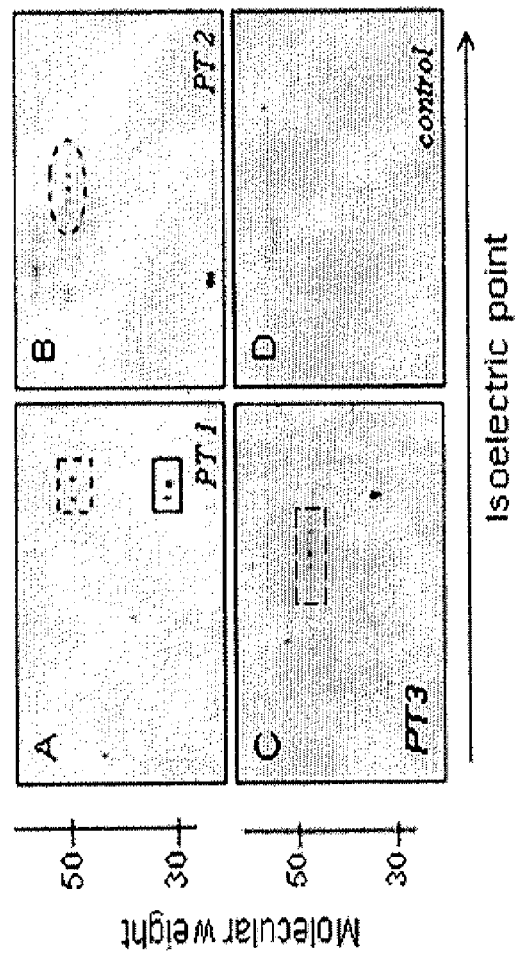
FIG. 6. Sera from women with unexplained infertility react with multiple proteins in two-dimensional Western blots. Examples of sera (1:200 dilution) reactions of three different patients (PT 1-3) are shown (Panels A-C). A control incubation with human ovarian protein in which patient sera was omitted (second antibody control) shows no significant reaction (Panel D). Panel A: Upper spot at about 50 kDa shows a-enolase (dotted box). Lower spot shows glyceraldehyde-3-phosphate dehydrogenase reaction at 36 kDa (solid box). Panel B: Spots at about 50 kDa correspond to aldehyde dehydrogenase (dotted oval). Panel C: spots at about 50 kDa correspond to Selenium Binding Protein 1 (dotted box).
Figure 7:
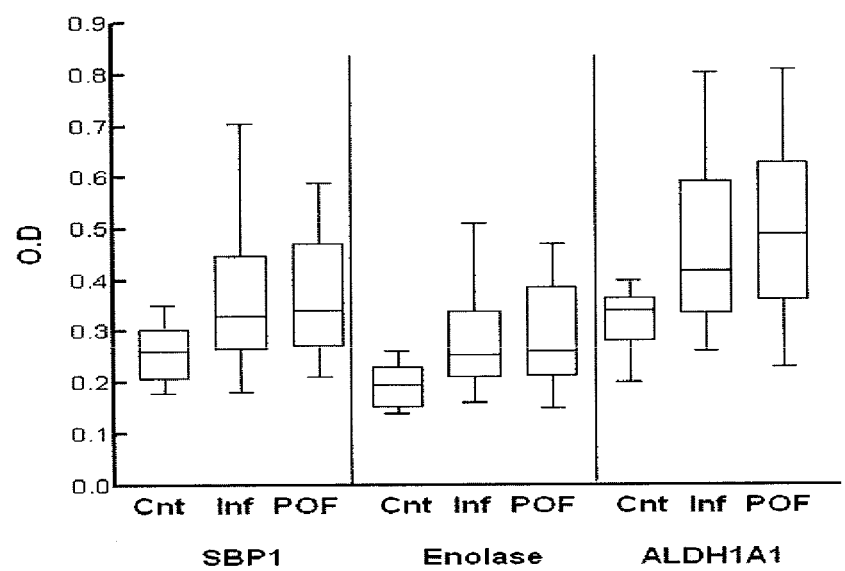
FIG. 7: Immunoassay of patient sera against recombinant SELENBP1, Enolase and ALDH1A1. The box plot shows the median (horizontal line), data in the 50th percentile (box) and data range (T-bars) of the optical density (OD) values for control sera (Cnt), infertility sera (Inf) and premature ovarian failure (POF) sera for each protein. The OD values differed significantly from controls for infertility (SELENBP1, $p=0.020$; enolase, $p=0.009$; ALDH1A1, $p=0.026$) and POF (SELENBP1, $p=0.019$; enolase, $p=0.009$; ALDH1A1, $p=0.019$). There was no significant difference between OD density values for infertility and POF for each protein ($p>0.6$). Applying the OD cutoff value for a positive antibody result based on the control mean OD (0.37 for SELENBP1; 0.28 for enolase; 0.46 for ALDH1A1), infertility and POF sera were positive for SELENBP1 (55%), enolase (40%) and ALDH1A1 (52.5%). 80.7% (n=21/26) of sera positive for AOA, but only 7% (1/14) of those originally negative for AOA had autoantibodies to one or more of the three antigens.
Figure 8:
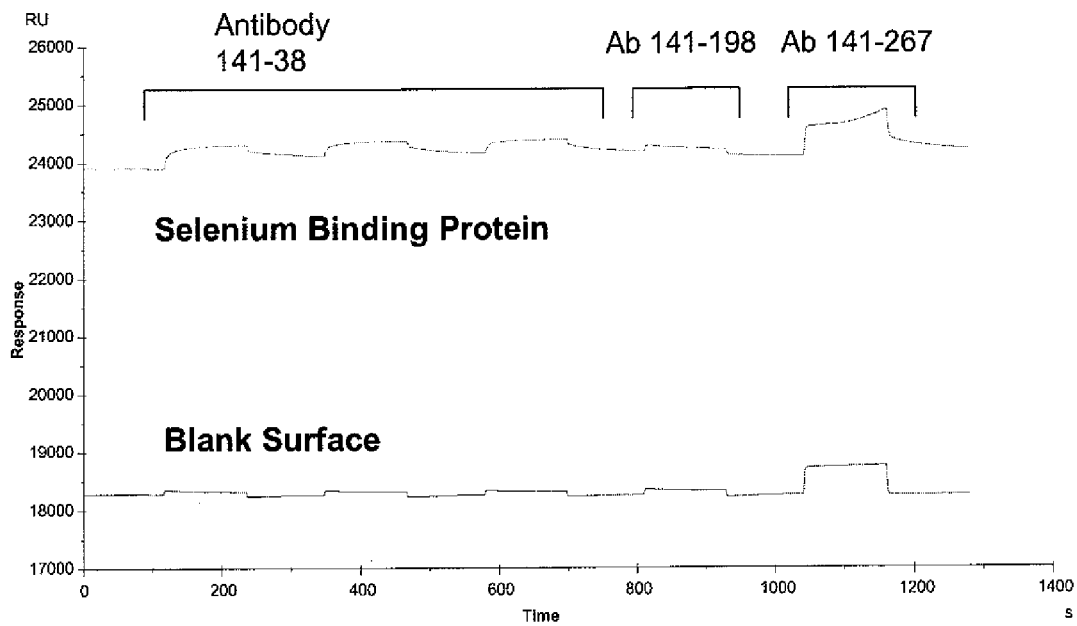
FIG. 8 shows the sensorgrams for two separate flow-cells, one with the SBP attached and the other with no protein attached. Antibodies bound to the SBP flow-cell, but did not bind to the blank surface cell. The square wave pattern on the blank cell is the result of buffer differences between the sample and flow running buffer.
Figure 9:
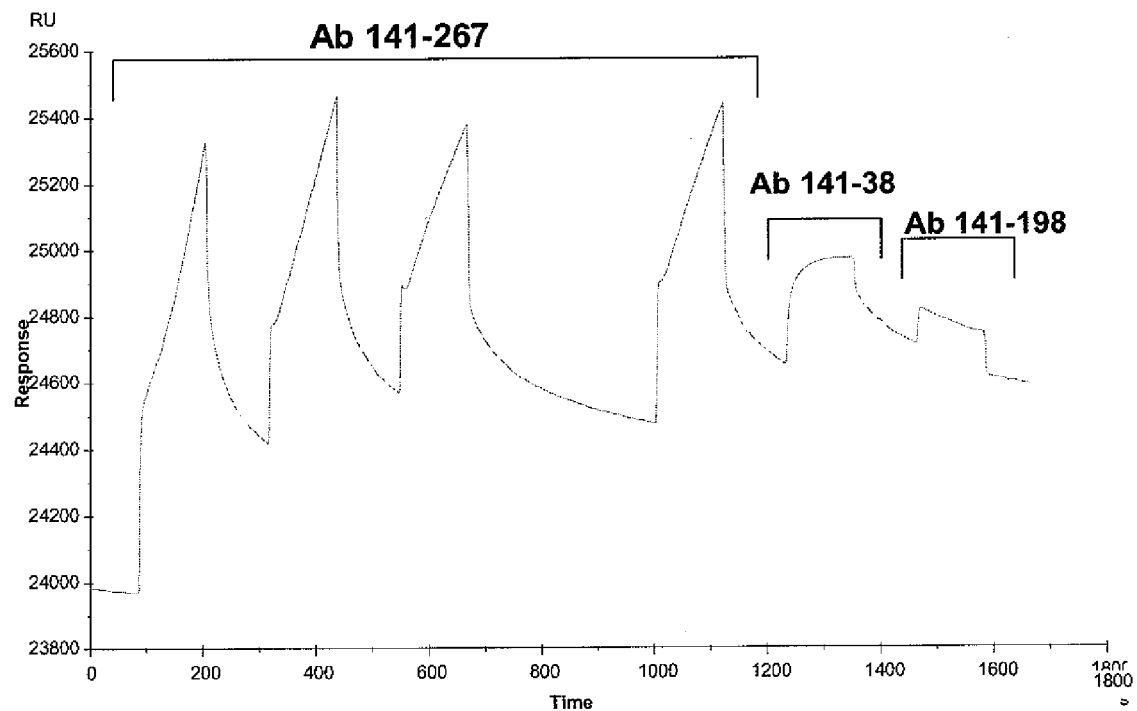
FIG. 9 is a sensorgram of the flowcell with SBP bound. Antibody 141-267 was loaded to near saturation, followed by sequential injection of antibodies 141-38 and 141-198. The results indicate binding by antibodies 141-267 and 141-38, but not Ab 141-198.

FIG. 4 shows a summary of the frequency of antigen reactions in Infertility, Ovarian cancer (OvCa) and benign gynecology/tumor controls (benign) detected by ELISA (1:100) as shown in FIG. 3. Benign controls have antibodies to either no or 1 antigen; OvCa and Infertility tend to have antibodies to multiple antigens. The ELISA method is the same as used for FIG. 3.

The examples and materials and methods described provides an immunoassay that measures the presence or concentration of an anti-SELENBP1, an anti-ALDH autoantibody (anti-ALDH1A1, anti-ALDH3A1) autoantibody in a biological sample of a mammal, wherein the immunoassay includes the steps of contacting the biological sample with an antigen specific for an anti-SELENBP1 or anti-ALDH autoantibody, or other suitable antibodies such as those described herein, the contacting being under conditions sufficient to permit anti-SELENBP1, anti-ALDH1A1, anti-ALDH3A1 autoantibody—if present in the sample, to bind to the antigen and form an antigen-anti-SELENBP1 and/or antigen—anti-ALDH1A1 and/or antigen-anti-ALDH3A1 autoantibody complex; (c) determining the presence or concentration of the autoantibody in the biological sample by determining the presence or concentration of the formed extended complex; (d) using the information obtained to determine the presence or absence of an ovarian disorder. The information obtained may be used to direct a patient for confirming diagnostic or treatments. Methods of treatment for reproductive health and/or ovarian disease include any that are known in the art, approved by regulatory agencies or in development.

Recombinant and purified proteins were produced for SELENBP1, ALDH1, ALDH3, mesothelin, vimentin and enolase (as well as GAPDH, PDIA3, CYP17 and others).

It is contemplated that the components of the immunoassay can be provided in kit form such that the assay can be done anywhere it is required. It is further contemplated that the kit can contain additional information such as a chart or table to correlate the data obtained with an appropriate treatment protocol. Finally, it is contemplated that the diagnostic assay described herein could be used in combination with other assays and diagnostic tests as known in the art to improve the diagnosis or prognosis of a patient.

The previous examples and embodiments are not meant to limit the invention and additional alternatives would be possible to one of ordinary skill in the art based on the above description.

Definitions and Abbreviations

As used herein and in the claims, the singular forms "a", "an", and "the" include plural reference unless the context clearly dictates otherwise. Thus, for example, reference to an "antibody" is a reference to one or more antibodies and equivalents thereof known to those skilled in the art, and so forth. Similarly, reference to an "autoantibody" is reference to one or more autoantibodies and equivalents thereof which are directed against an individual's own proteins.

As used herein, the term "anti-SELENBP1", "anti-SBP1" or "anti-SeBP1" antibody is defined as an antibody that is capable of binding to Homo sapiens selenium binding protein 1 or a peptide generated therefrom, which nucleotide coding sequence using the single letter codes is found in SEQ ID NO: 1 and whose corresponding amino acid sequence using the single letter codes that are common for amino acids is generated from the mRNA sequences, as is well known to those of ordinary skill in the art, and which are found in SEQ ID NO: 2.

As used herein the term "anti-ALDH antibody" or "anti-ALDH" is defined as an antibody that is capable of binding to a Homo sapiens Aldehyde Dehydrogenase family member or a peptide generated therefrom.

As used herein the term "anti-ALDH1A1 antibody" or "antiALDH1A1" is defined as an antibody that is capable of binding to Homo sapiens Aldehyde Dehydrogenase 1 family member A1 or a peptide generated therefrom the nucleotide coding sequence of which using the single letter codes is found in SEQ ID NO: 3 and whose corresponding amino acid sequence using the single letter codes that are common for amino acids is generated from the mRNA sequences, as is well known to those of ordinary skill in the art, and which are found in SEQ ID NO: 4.

As used herein the term "anti-ALDH3A1 antibody" or "antiALDH3A1" is defined as an antibody that is capable of binding to Homo sapiens Aldehyde Dehydrogenase 3 family member A1 or a peptide generated there from which nucleotide sequence using the single letter codes is found in SEQ ID NO: 5 and whose corresponding amino acid sequence using the single letter codes that are common for amino acids is generated from the mRNA sequences as is well known to those of ordinary skill in the art and which are found in SEQ ID NO: 6.

As used herein the term SBP has 472 amino acids with theoretical MW of 52.3 kD and PI 6.5 (SEQ ID NO: 2).

As used herein the term ALDH1A1: has 501 amino acids with theoretical MW of 54.9 kD and PI 6.7 (SEQ ID NO: 4).

As used herein the term ALDH3A1: has 453 amino acids with theoretical MW of 50.4 kD and PI 6.11 (SEQ ID NO: 6).

As used herein "diagnosing", in its various grammatical forms, is defined as identifying a disease state, disease progression, or other abnormal condition, based upon symptoms, signs, and other physiological and anatomical parameters.

As used herein "peptide", in its various grammatical forms, is defined in its broadest sense to refer to a compound of two or more subunit amino acids, amino acid analogs, or other peptidomimetics. The subunits may be linked by peptide bonds or by other bonds, for example ester, ether, and the like. As used herein, the term "amino acid" refers to either natural and/or unnatural or synthetic amino acids, including Glycine and both the D or L optical isomers, and amino acid analogs and peptidomimetics. If the peptide chain is short, e.g. three or more amino acids, it is commonly called an oligopeptide. If the peptide chain is longer, the peptide is typically called a polypeptide or a protein. Full-length proteins, analogs, mutants and fragments thereof are encompassed by the definition. The terms also include postexpression modifications of the polypeptide, for example, glycosylation, acetylation, phosphorylation and the like. Furthermore, as ionizable amino and carboxyl groups are present in the molecule, a particular peptide may be obtained as an acidic or basic salt, or in neutral form. A peptide may be obtained directly from the source organism, or may be recombinantly or synthetically produced.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described.

EXAMPLE 1

Ovarian Autoantigens are Associated with Ovarian Autoantibodies

Patients: 74 patients with infertility, 19 patients with premature ovarian failure, 16 healthy control women.

Identification of autoantigens.

Results: In order to identify major antigens for ovarian autoimmunity, 74 sera from women with unexplained infertility were screened for ovarian autoantibodies (AOA) by immunoassay and one-dimensional Western blot. The majority of sera had immuno-reactions at 50-56 kDa. Six representative positive infertility sera were used to identify antigens between 40-60 kD by two-dimensional Western blot and mass spectrometry. Antigens included aldehyde (retinal) dehydrogenases (ALDH1A1, ALDH1A2, ALDH7A1), protein disulfide-isomerase A3 (PDIA3), vimentin (VIME), α-enolase (ENO1), phosphoglycerate dehydrogenase and selenium binding protein 1 (SBP1). 60% (n=24/40) of infertility and POF sera were positive for recombinant ALDH1A1, SBP1 or enolase. 80.7% (n=21/26) of AOA positive sera had antibodies to one or more of the three antigens, while only 7% (n=1/14) of AOA negative sera had antibodies to recombinant proteins. ALDH1A1 and SBP1 are unique to ovarian autoimmunity associated with infertility and POF, and may provide the basis for specific tests to identify patients with ovarian autoimmunity.

The objective was to identify candidate autoantigens using immuno-proteomics. In order to focus the identification of antigens on the more frequent immunoreactions, the predominant immunoreactions of sera with ovarian proteins were determined using sera from women with unexplained infertility. Selected recombinant autoantigens were then tested for reaction with both infertility and POF sera to confirm their reaction with these autoantigens.

Materials and Methods

Patients

Patients at Rush University Medical Center and the University of Ulm were enrolled following protocols approved by the respective Institutional Review Boards. Unexplained infertility patients (n=74) had normal results on standard clinical evaluation, including a normal semen analysis, postcoital test, ovulation (luteal phase progesterone) and tubal patency. Patients with unexplained infertility were 31.0±4.1 years old and had normal day 3 FSH levels (6.5±1.9 mIU/ml). TSH levels were normal (1.4±1.1 IU/mL). The average duration of infertility was 3.2±2.0 years. The average number of prior in vitro fertilization (IVF) cycles was 1.0±1.1. Premature ovarian failure patients (POF) (n=19) had an average age of 30.7±6.6 years and experienced menopause at an average age of 26.6±9.1 years. FSH levels were elevated (64.0±37.8 mIU/mL). TSH levels were normal (1.2±1.1 IU/mL). Only two patients had previous hormone stimulation (for IUI) and none had IVF. Control sera (n=16) were obtained from normally cycling women or postmenopausal women without a history of diagnosed infertility or autoimmune disease and were 35.6±10.6 years old.

Serum and Tissue

Blood was collected into a red top tube and the separated serum was stored (−70° C.). Normal human ovaries removed at hysterectomy were obtained through the National Disease Research Interchange (Philadelphia, Pa.). The ovaries used for immunoassay and gel electrophoresis were from women with an average age of 47.7±4.2 years.

Tissue from three ovaries was pooled and homogenized as described previously (Luborsky, et al., J Clin Endocrinol Metab, 1990. 70(1): 69-75) resulting in a 1,000×g supernatant (Barua, et al., International Journal of Gynecological Cancer, 2009. 19(4): 500-507; Am J Reprod Immunol, 2007. 57: 243-249). The supernatant (0.5 ml/500 mg tissue weight) was incubated with protein-G/magnetic bead complexes (30 minutes, 20° C.) (Miltenyi Biotech) to remove excess immunoglobulin. The protein content of the supernatant was measured (Bradford assay; BioRad) with bovine serum albumin (BSA) as a standard (Sigma).

The homogenate was used to coat the wells of immunoassay plates (200 ug/well/0.1 mL phosphate buffer, pH 7.0). Sera were screened for AOA using the previously described assay (Luborsky, et al., J Clin Endocrinol Metab, 1990. 70(1): 69-75; Hum Reprod, 2002. 17(10): 2641-9). Optical density (OD) values two standard deviations (SD) greater than the control mean were considered positive (p<0.05).

Gel Electrophoresis and Western Blot

For one-dimensional gel electrophoresis (1-DE), the ovarian extract was mixed with SDS-PAGE lysis buffer (2% SDS, 25% glycerol, 62.5 mM Tris-HCl, pH 6.8). Protein (250 µg/gel) was resolved in discontinuous 10% Tris-HCl SDS-PAGE preparative well gels (BioRad) with a molecular weight standard (MagicMarker Mix, Invitrogen), and stained with Sypro Ruby (Invitrogen). Digital images were obtained with a Chemidoc XRS Imaging System (BioRad).

For two-dimensional gel electrophoresis (2-DE), proteins were passively rehydrated into IPG strips (16 hours, 20° C.) in rehydration buffer and focused as described previously. Each IPG strip was loaded on a 10% SDS-Tris HCl gel and resolved as for 1-DE.

For 1-DE or 2-DE Western blot, proteins were transferred (13V, 25 minutes) to nitrocellulose (0.45 µm; BioRad), and blots blocked overnight (16 hours, 4° C.) in Tris buffered Starting Block (Pierce) containing 0.05% Tween-20. For 1-DE, the blot was transferred to a multiscreen apparatus (BioRad) according to the manufacturer's instructions. Sera (1:100) were applied (1 hour, 22° C.), the blot removed, washed and incubated with horseradish peroxidase conjugated goat anti-human immunoglobulin (1:10,000, 1 hour, 22° C.; Jackson ImmunoResearch). For 2-DE Western blots the blots were blocked and washed as above, and incubated in serum (1:500). The chemiluminescence reaction was visualized with SuperSignal West Dura Extended Duration substrate (Pierce) and the image analyzed as above.

The molecular sizes of bands in 1-DE Western blots were estimated with QuantityOne and PDQuest software (BioRad) for frequency analysis. Gel images were analyzed to determine Rf values of bands. The molecular weight of each band was calculated from a standard Rf curve generated from the molecular weight standards. Rf values were normalized to a positive sera included in every blot. Previous immunoassays used either rat or human ovarian proteins (correlation coefficient=0.9, p<0.001) and both human and rat ovarian proteins were used for frequency analysis with identical results using GraphPad Prism (v3) software.

Mass Spectrometry and Protein Identification

Six representative sera were used to identify antigens. Two to three 2-DE Western blots per serum (15 total) were used to develop spot summaries to locate immunoreactive protein in gels. Proteins were excised, trypsin (Pierce) digested and peptides microsequenced bLC MS/MS using a C18 ProteoPrep nano-HPLC column attached to a NewObjective nano-ESI source interfaced to a ThermoFinnigan LTQ ion trap mass spectrometer. MS/MS spectra for m/z 440-2000 were obtained using ESI voltage 2.1 kV, MS/MS, isolation width 1.5 m/z, activation Q 0.25, activation time 30 msec and collision energy 35%. Peptide sequence identified with SEQUEST and was searched against human proteins in GenBank v.156. The proteins were ranked according to their protein score. The criteria for selection were proteins with a molecular weight of approximately 50 kDa, with greater than 10 Flicka hits (4 peptide sequence hits or more has a 95% confidence level) and a sequence coverage of more than 25%.

Recombinant Protein Immunoassays

Recombinant proteins were produced by expressing the full length mRNA expression ready clone using the PET28 Expression vector in *E. coli*. Histidine-tagged protein was purified using a Ni-NTA (Qiagen) column, eluted with 200 mM imidazole, and further purified by size exclusion chromatography (Superdex 200 16/60; Pharmacia) and ion exchange (Hi-Trap Q column; Pharmacia). The purity of the recombinant protein was verified by 2-DE.

Immunoassays were performed by standard methods. In summary, immunoassay plates (Nunc Maxisorp) were coated (16 hours, 4° C.) with recombinant protein (50 ng/well) in carbonate buffer (50 mM, pH 9.7). Plates were washed with PBS (pH 7.4) containing 0.05% TritonX-100 and nonspecific binding sites were blocked with PBS containing 5% BSA (1 hour, 22° C.). Patient sera were diluted (1:100/0.1 mL/well) in PBS containing 1% BSA, incubated (90 minutes, 22° C.), and autoantibody detected with goat anti-human FAB specific-alkaline phosphatase (AP) (Sigma) reacted with AP substrate (Sigma). OD values (405 nm) greater than 2SD above the mean control OD value were considered positive (p<0.05). The Student's t-test with equal variance was used to identify significant differences.

Results

Frequency Distribution of Immunoreactive Bands

Sera positive for AOA (68%, 50/74) reacted with bands from 20 kD-110 kD with an average of 4.1±1.5 (SD) bands per serum in 1-DE Western blots 74% of the immunoreactions occurred at 50-56 kDa. Six representative infertility sera that exhibited typical reactions at 40-60 kD were selected for 2-DE Western blots and antigen identification.

Identification of Autoantigens Using Infertility Sera

Similar to 1-DE blots, there was a predominance of reactions around 50 kDa in 2-DE Western blots. Proteins with a molecular weight of 40-60 kD identified using micro-sequencing included aldehyde dehydrogenase family members (ALDH1A1, ALDH1A2, ALDH7A1), Selenium Binding Protein 1 (SBP1), vimentin, α-enolase (ENO1), protein disulfide-isomerase A3 (PDIA3) precursor and D-3-phosphoglycerate dehydrogenase (3PGDH). Immunoreactive spots near 40 kD were also analyzed and contained annexin A2 (AnxA2; molecular weight 38.8 kD; 25 hits, 52% coverage), carbonic anhydrase 1 (CA1; molecular weight 28.8 kD; 9 hits, 49.5% coverage) and glyceraldehyde-3-phosphate dehydrogenase (GAPDH; molecular weight 36 kD; 15 hits, 41% coverage).

Reaction of Infertility and POF Sera with Selected Recombinant Proteins

The two antigens that appear to be unique to ovarian autoimmunity, ALDH1A1 and SBP1, as well as α-enolase, were tested for reaction with both infertility (n=21) and POF (n=19) sera. The OD values for infertility and POF sera differed significantly from controls. Using the cutoff value based on controls, 55.0% (n=22/40) of sera had anti-SBP1 antibodies, 40% (n=16/40) had anti-enolase antibodies and 52.5% (n=21/40) of sera had anti-ALDH1A1 antibodies. Overall, 60% (24/40) had antibodies to one or more of the three antigens.

The data were further examined for significant differences between infertility and POF. There was no significant difference between OD values for infertility and POF sera for any of the antigens. The proportion of sera positive for individual antigens was similar for infertility and POF respectively (SBP1, 47.6% and 63.2%; enolase, 33.3% and 47.4%; ALDH1A1, 47.6% and 57.9%).

Based on anti-ovarian antibodies (AOA) immunoassay results (26 AOA positive, 14 AOA negative), 80.7% (n=21/26) of sera positive for AOA had antibodies to one or more of the three antigens. Only 7% (n=1/14) of sera negative for AOA had antibodies to any of the recombinant proteins.

Standard procedures are used to prepare antigen-Luminex bead complexes. Briefly, recombinant proteins are coupled directly to carboxylated beads or to an antibody to His6 (SEQ ID NO: 7) (recombinant proteins) bound to carboxylated beads according to the manufacturers specifications. Separate beads are prepared for each protein and a specific antibody to each antigen is used to verify protein coupling to beads. A training set of sera (n=5 positive for each antigen and 10 negative sera; total of 60 sera) selected using a direct ELISA in order to select test sera for the multiplex assay. Concentrations of protein (5, 10, 20, 30 ug) for bead coupling will then be evaluated with the training set for a maximum difference signal between the mean fluorescence intensity of positive and negative sera at a serum dilution of 1:50. Once the optimum protein is determined, sera titers of 1:25, 1:50, and 1:100 will be tested to determine the optimum overall serum dilution that with minimal signals in normal healthy control sera and maximum signals in positive test set sera.

Antibodies bound to the beads are detected with biotinylated anti-human immunoglobulin followed by phycoerythrin-conjugated streptavidin. Results are determined by comparison to a set of normal assay controls to determine a Mean Fluorescence Intensity (MFI) cutoff (2 standard deviations above the control mean value). Normal assay controls are used in all assays to assess serum background and are from apparently healthy subjects without autoimmune disease, cancer or a history of cancer.

Control beads include human immunoglobulin (to monitor the addition of biotin-conjugated-secondary antibody), albumin (an irrelevant protein), or vector alone (to control for bacterial contaminants in the antigen preparations) and uncoated beads (to assess nonspecific binding). If some proteins do not couple well, alternatives are other protein preparations or commercial sources. Sera are assayed against individual beads and then the beads are mixed to determine if there are any interactions that change the result. For example, mesothelin is known to bind to CA125. If there is an interaction effect, beads will used in two batches to keep interacting proteins/antibodies separate.

Materials and Methods Antibody Production

Polyclonal Antibody Production

Longhorn chicken was injected three times with purified recombinant selenium binding protein (SBP). Initial injection was with 500 ug of protein mixed with Titermax adjuvant and two booster injections were given with 250 ug of protein mixed with Freunds Incomplete Adjuvant with three week intervals between the injections. The chicken was test bleed after two weeks from the last booster dose and tested for antibody titter. The egg from the chicken were collected for 14 days, egg yolk is separated and chicken immunoglobin IgY was extracted using polyethylene glycol chloroform extraction. In summary, egg yolk is diluted with Phsphate buffer 1:2 ratio and separated the soluble protein using chloroform (1:1). IgY were precipitated from the supernatant by adding equal volume of 24% w/v PEG8000. The extracted antibody was tested against the rec SBP protein in ELISA and western blot.

Monoclonal Antibody Producton

Mice were injected with recombinant SBP and tested for antibody titter. The mice spleen cells were fused with myeloma cells and selectively enriched in medium contain HAP. The individual clones were screen for SBP antibody titter using ELISA and three clones (#141-38, #141-198 and #141-267) were selected based on the antibody titter and scaled up for large scale production of the antibody. The antibody was purified by HPLC and eluted by 0.1M Glycine, pH2.8 and immediately neutralized by 1M Tris-base. Using Biacore the epitope cross matching was done and it was found that the clones have distinctive binding epitopes but a small overlap between antibody #141-38 and #141-198. The extracted antibody were tested against the rec SBP protein in ELISA and western blot.

TABLE 1

Autoantigens (40-60 kD) identified from human ovary using LC-MS/MS

| Identity | AC | Mw (kD) | pI | Coverage (%) | Flicka hit |
|---|---|---|---|---|---|
| Aldehyde dehydrogenase 1A1 | AAH01505 | 54.8 | 6.3 | 38.8 | 27 |
| Aldehyde dehydrogenase 1A2 | ABC40749 | 56.7 | 5.8 | 40.5 | 14 |
| Aldehyde dehydrogenase 7A1 (Antiquitin) | AAH02515 | 58.7 | 6.3 | 27.9 | 13 |
| Alpha-Enolase | CAA34360 | 47.1 | 7.3 | 65.0 | 31 |
| Phosphoglycerate dehydrogenase | AAH00303 | 56.6 | 6.3 | 25.4 | 13 |

TABLE 1-continued

Autoantigens (40-60 kD) identified from human ovary using LC-MS/MS

| Identity | AC | Mw (kD) | pI | Coverage (%) | Flicka hit |
|---|---|---|---|---|---|
| Protein disulfide-isomerase A3 | BAA11928 | 56.8 | 6 | 67.7 | 40 |
| Selenium-binding protein 1 | AAH09084 | 52.4 | 6.1 | 44.9 | 20 |
| Vimentin | AAH00163 | 53.6 | 5 | 61.0 | 30 |

Abbreviations:
LC-MS/MS = high pressure liquid chromatography coupled tandem mass spectrometry;
AC = accession number in GenBank;
Mw = molecular weight;
pI = isoelectric point;
Coverage = the percent of peptide sequences matched;
Flicka hit = the number of unique peptide matches

TABLE 2

Anti-SBP1 and Anti-Mesothelin are Not Correlated with CA125

| CA125 VS | Correlation coefficient | P value |
|---|---|---|
| Anti-SBP1 | 0.01 | 0.9 |
| Anti-Mesothelin | 0.04 | 0.7 |
| Circulating Mesothelin | 0.27 | 0.001 |
| Anti-p53 | 0.24 | 0.02 |
| CRP | 0.24 | 0.003 |

TABLE 3

Antibodies to SBP1 are Specific for Infertility & Ovarian Cancer
Selenium Binding Protein 1 (SBP1) Antibody
in Infertility and Ovarian Cancer

| | OD value Mean ± SD (range) | % POS (2SD) % (n/total) |
|---|---|---|
| NORMAL | 0.53 ± 0.21 (0.16-0.99) | 3.3% (1/30) |
| INFERTILITY PATIENTS | | |
| ENDOMETRIOSIS | 0.67 ± 0.19 (0.27-1.02)* | 5.6% (1/18) |
| OVULATORY DYSFUNCTION | 0.87 ± 0.24 (0.55-1.30)*** | 50% (6/12)** |
| UNEXPLAINED INFERTILITY | 0.68 ± 0.25 (0.38-1.31)* | 24% (9/37)* |
| PREMATURE OVARIAN FAILURE | 0.68 ± 0.28 (0.28-1.35) | 28% (7/25)* |
| BENIGN TUMOR OR CYST | 0.57 ± 0.16 (0.31-0.88) | 0% (0/23) |
| OTHER CANCER | 0.58 ± 0.17 (0.27-0.97) | 4.8% (1/21) |
| OVARIAN CANCER | 0.69 ± 0.37 (0.22-1.93) | 18% (6/33) |
| ASSAY SERUM CONTROL | 0.67 ± 0.13 (0.49-0.83) | ref |

Significance indicated
*P = 0.05-0.01;
**P = 0.01-0.001;
***P < 0.001 vs. normal healthy controls

The invention claimed is:

1. A method to determine the presence and concentration of anti-SELENBP1 autoantibodies in a biological sample from an individual suspected of having ovarian cancer, comprises:
   (a) contacting the biological sample with antigen SELENBP1 or a fragment thereof in conditions where naturally occurring autoantibodies form antigen antibody complexes with the antigen provided;
   (b) determining the presence and concentration of anti-SELENBP1 autoantibodies in the biological sample by analysis of the complexes; and
   (c) comparing the presence and concentration of anti-SELENBP1 autoantibodies determined in (b) with values in biological samples from subjects without ovarian cancer; and
   (d) inferring that ovarian cancer is present in the individual, if anti-SELENBP1 autoantibodies are present in a concentration that is higher than the concentration in the subjects without ovarian cancer.

2. The method of claim 1 wherein SELENBP1 is a recombinant protein.

* * * * *

UNITED STATES PATENT AND TRADEMARK OFFICE
CERTIFICATE OF CORRECTION

| | | |
|---|---|---|
| PATENT NO. | : 8,722,351 B2 | Page 1 of 1 |
| APPLICATION NO. | : 13/496418 | |
| DATED | : May 13, 2014 | |
| INVENTOR(S) | : Judith Luborsky et al. | |

It is certified that error appears in the above-identified patent and that said Letters Patent is hereby corrected as shown below:

In the Specification

In column 1, the paragraph beginning at line 17 should read as follows:

The present invention was made in part with U.S. government support under grant number 1RO1 AI 055060-01 awarded by the National Institutes of Health. The U.S. Government has certain rights in the invention.

Signed and Sealed this
Seventeenth Day of February, 2015

Michelle K. Lee
*Deputy Director of the United States Patent and Trademark Office*

UNITED STATES PATENT AND TRADEMARK OFFICE
CERTIFICATE OF CORRECTION

PATENT NO.      : 8,722,351 B2                      Page 1 of 1
APPLICATION NO. : 13/496418
DATED           : May 13, 2014
INVENTOR(S)     : Judith Luborsky et al.

It is certified that error appears in the above-identified patent and that said Letters Patent is hereby corrected as shown below:

In the specification

In column 1, the paragraph beginning at line 17 should read as follows:

--This invention was made with government support under grant number AI055060 awarded by the National Institutes of Health. The government has certain rights in the invention.--

Signed and Sealed this
Fifth Day of April, 2016

Michelle K. Lee
*Director of the United States Patent and Trademark Office*